US010041050B2

(12) United States Patent
Adielsson et al.

(10) Patent No.: US 10,041,050 B2
(45) **Date of Patent: *Aug. 7, 2018**

(54) METHOD FOR ENDOTOXIN REMOVAL

(71) Applicant: GE Healthcare BioProcess R&D AB, Uppsala (SE)

(72) Inventors: Patrik Adielsson, Uppsala (SE); Tobias E. Soderman, Uppsala (SE); Anna Akerblom, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/355,675

(22) Filed: Nov. 18, 2016

(65) Prior Publication Data

US 2017/0067031 A1 Mar. 9, 2017

Related U.S. Application Data

(63) Continuation-in-part of application No. 14/380,477, filed as application No. PCT/SE2013/050176 on Feb. 27, 2013, now Pat. No. 9,580,692.

(30) Foreign Application Priority Data

Feb. 29, 2012 (SE) ...................................... 1250181

(51) Int. Cl.
*B01D 15/38* (2006.01)
*C12N 7/00* (2006.01)
*C12N 7/02* (2006.01)

(52) U.S. Cl.
CPC ........... *C12N 7/00* (2013.01); *B01D 15/3847* (2013.01); *C12N 2760/16151* (2013.01)

(58) Field of Classification Search
CPC .. B01D 15/3847; B01D 15/363; B01J 20/285; B01J 20/3244; B01J 20/3268; B01J 20/3274; B01J 20/3285; B01J 20/3289; B01J 20/3293; B01J 20/24; B01J 20/286; B01J 20/281; B01J 20/3242; C12N 2760/16151; C12N 7/00; C07K 1/20
See application file for complete search history.

(56) References Cited

U.S. PATENT DOCUMENTS 5,187,066 A 2/1993 Becker
5,917,022 A 6/1999 Davies
6,780,327 B1 8/2004 Wu et al.
6,803,183 B2 10/2004 Amoureux et al.
7,858,341 B2 12/2010 Reardon et al.
9,580,692 B2 2/2017 Adielsson et al.
2007/0213258 A1 9/2007 Nakayama et al.

FOREIGN PATENT DOCUMENTS

EP 2336304 A1 6/2011
WO 2004/036189 A2 4/2004
WO 2006/063362 A1 6/2006
WO 2009/131526 A1 10/2009
WO 2013/130001 A1 9/2013

OTHER PUBLICATIONS

International Search Report and Written Opinion Received for PCT Patent Application No. PCT/SE2013/050176, dated Jun. 5, 2013, 12 Pages.
International Preliminary Report on Patentability Received for PCT Patent Application No. PCT/SE2013/050176, dated Sep. 12, 2014, 8 Pages.
Non-Final Office Action Received for U.S. Appl. No. 14/380,477, dated Dec. 9, 2015, 8 Pages.
Final Office Action Received for U.S. Appl. No. 14/380,477, dated Jun. 2, 2016, 12 Pages.
Notice of Allowance Received for U.S. Appl. No. 14/380,477, dated Sep. 30, 2016, 9 Pages.
McNeff et al. "The Efficient Removal of Endotoxins From Insulin Using Quaternized Polyethyleneimine-Coated Porous Zirconia", Analytical Biochemistry, Oct. 15, 1999, vol. 274, pp. 181-187.
Hirayama et al. "Chromatographic Removal of Endotoxin From Protein Solutions by Polymer Particles", Journal of Chromatography, Dec. 5, 2002, vol. 781, No. 1-2, pp. 419-432.
Petsch et al. "Endotoxin Removal From Protein Solutions", Journal of Biotechnology, Jan. 21, 2000, vol. 76, pp. 97-119.
Sigma-Aldrich, Sigma-Aldrich Catalog, Searched by 2016.

*Primary Examiner* — Bao Q Li
(74) *Attorney, Agent, or Firm* — Wood IP LLC

(57) ABSTRACT

The present invention relates to a method for endotoxin removal from a sample comprising the following steps: combining the sample comprising one or more target molecule(s) with a chromatography media comprising beads having an inner porous core functionalized with ligands capable of binding endotoxin and an outer porous layer without functional groups and a pore size small enough to exclude the target molecule from the inner core; and collecting the sample from the media, wherein the sample comprises an endotoxin level which is at least 75% less, preferably 90% less, than before the removal and the yield of the target molecule is at least 75%.

20 Claims, 1 Drawing Sheet

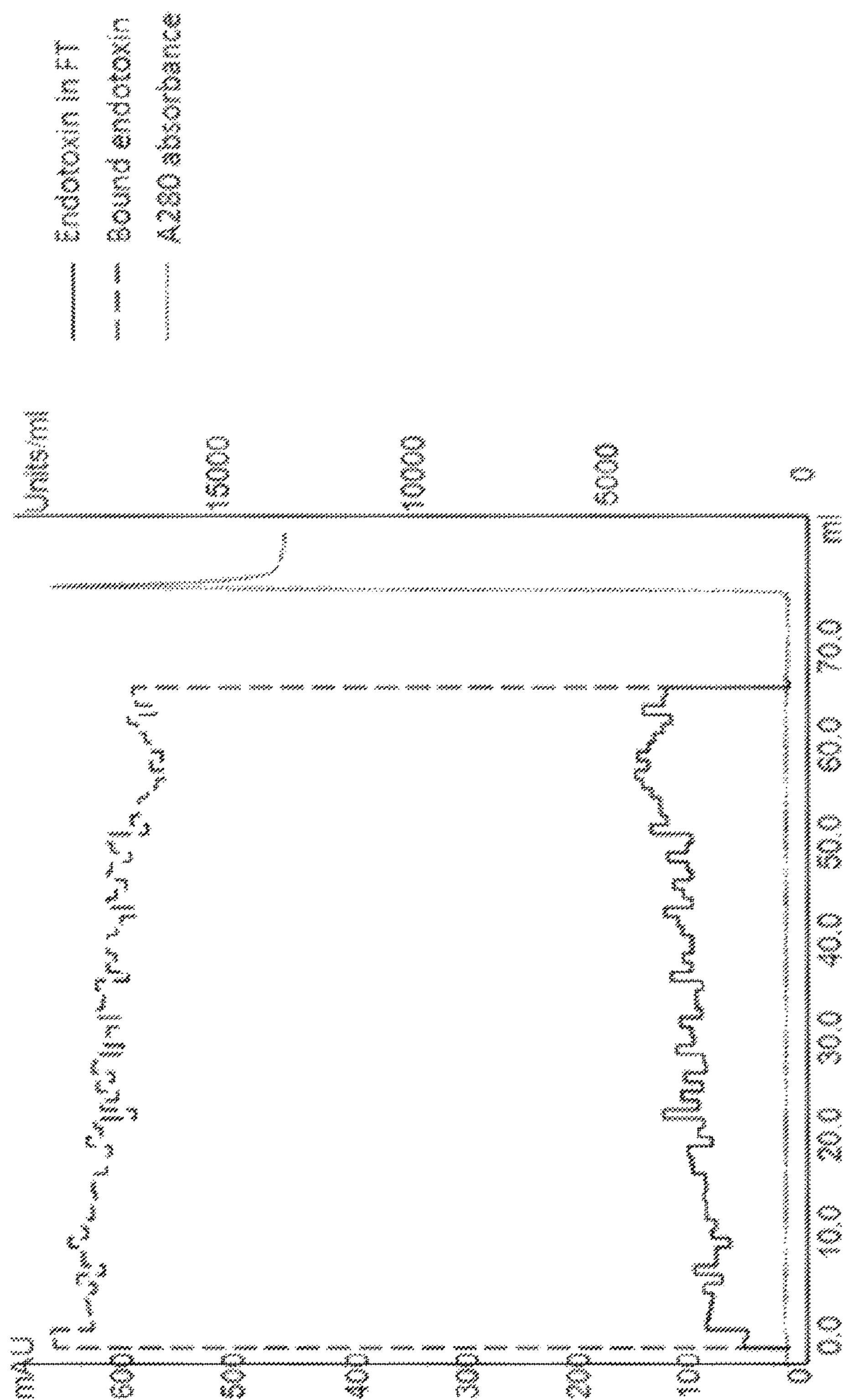
Endotoxin in FT
Bound endotoxin
A280 absorbance
Units/ml
15000
10000
5000
0
mAU
600
500
400
300
200
100
0
0.0
10.0
20.0
30.0
40.0
50.0
60.0
70.0
ml

METHOD FOR ENDOTOXIN REMOVAL

FIELD OF THE INVENTION

The present invention relates to a method for endotoxin removal. More closely it relates to a method for endotoxin removal by chromatography using specifically designed beads having an inner porous core and an outer porous layer with different properties than in the inner core.

BACKGROUND OF THE INVENTION

Endotoxins are lipopolysaccharides (LPS) derived from cell membrane of Gram-negative bacteria and are responsible for its organization and stability. Within the pharmaceutical industry, endotoxins may be present during production processes or in the final product. Although endotoxins are linked within the bacterial cell wall, they are continuously liberated into the environment. This liberation does not happen only with cell death but also during growth and division. Endotoxins are found almost everywhere since bacteria can grow in nutrient poor media, such as water, saline, and buffers. A single *Escherichia coli* contains about 2 million LPS molecules per cell. Endotoxin elicits a wide variety of pathophysiological effects. In conditions where the body is exposed to LPS excessively or systemically (as when small concentrations of LPS enter the blood stream), a systemic inflammatory reaction can occur, leading to multiple pathophysiological effects, such as endotoxin shock, tissue injury, and death. However, endotoxin does not act directly against cell or organs but through activation of the immune system, especially through monocytes and macrophages, with the release of a range of pro-inflammatory mediators, such as tumor necrosis factor (TNF), interleukin (IL)-6 and IL-1. Pyrogenic reactions and shock are induced in mammals upon intravenous injection of endotoxin at low concentrations (1 ng/mL). The maximum level of endotoxin for intravenous applications of pharmaceutical and biologic product is set to 5 endotoxin units (EU) per kg of body weight per hour by all pharmacopoeias. The term EU describes the biological activity of an endotoxin. For example, 100 pg of the standard endotoxin EC-5 and 120 pg of endotoxin from *Escherichia coli* 0111:B4 have activity of 1 EU. Meeting this threshold level has always been a challenge in biological research and pharmaceutical industry.

Within biotechnology industry, Gram-negative bacteria are widely used to produce recombinant DNA products such as peptides and proteins. Many recombinant proteins are produced by the Gram-negative bacteria *Escherichia coli*. These products will always be contaminated with endotoxins. For this reason, proteins prepared from Gram-negative bacteria must be as free as possible of endotoxin in order not to induce side effects when administered to animals or humans. However, endotoxins are very stable molecules, resisting to extreme temperatures and pH values in comparison to proteins.

Endotoxins are negatively charged substances and are also usually slightly hydrophobic.

Many different processes have been developed for the removal of LPS from proteins based on the unique molecular properties of the endotoxin molecules. These include LPS affinity resins, two-phase extractions, ultrafiltration, hydrophobic interaction chromatography, ion exchange chromatography, and membrane adsorbers.

One of the most commonly used techniques for endotoxin removal from a target protein sample is anion exchange chromatography. Since the endotoxin is negatively charged it binds strongly to the positively charged ligands of the anion exchange material. This method is however hampered with several drawbacks: If the protein to be purified is also negatively charged the binding conditions must be carefully adjusted to avoid coelution of endotoxin and target protein. Even after such an optimisation such a step is usually accompanied by a loss of product.

If the protein is positively charged the protein may be collected in the flowthrough in an anion exchange step but often association of the positively charged protein and the negatively charged endotoxin leads to less effective endotoxin removal and the equilibrium between binding of endotoxin between the target protein and the anion exchange needs to be carefully studied.

In U.S. Pat. No. 5,917,022, a method of endotoxin removal is described that involve contacting the sample with Sephacryl gel filtration media. Gel filtration media interact very weakly with proteins but according to the patent the endotoxins bind to the gel filtration particles. However, the binding capacity of the Sephacryl media is very low due the fact that no endotoxin binding ligands are attached.

In U.S. Pat. No. 6,803,183, an endotoxin removal method is disclosed where a support material containing hydrophobic amines in combination with amines reacted with a hydroquinolone moiety is contacted with the sample in question to remove the endotoxins. However, the endotoxin removal is in the lower range from 25-84% removal and the conditions need to be optimised in order to avoid binding of the target molecule.

There is thus a need for a more robust step for endotoxin removal that requires less optimisation and where loss of target molecule can be avoided.

SUMMARY OF THE INVENTION

The present invention provides a new method using a separation material for endotoxin removal resulting in low residual levels of endotoxin after a separation procedure while maintaining a high yield of the target protein. The separation material has the following characteristics: no interaction with the target protein; strong affinity and sufficient binding capacity for endotoxin; able to be regenerated; and stable under normal operation conditions and regeneration conditions.

In a first aspect, the invention relates to a method for endotoxin removal from a sample comprising the following steps: combining the sample comprising one or more target molecule(s) with a chromatography media comprising beads having an inner porous core functionalized with ligands capable of binding endotoxin and an outer porous layer without functional groups and a pore size small enough to exclude the target molecule from the inner core; and collecting the sample from the media, wherein the sample comprises an endotoxin level which is at least 75% less, preferably 90% less, than before the removal and the yield of the target molecule is at least 75%.

The method is not restricted to the type of target molecule. The target molecule may be any protein, virus or cell. Preferably the target protein is a recombinant protein.

Preferably the chromatography media is packed in a column and the sample is collected in the flow-through. But the media may also be used in a batch mode. In this case the target molecule may be collected after the media has been filtered off.

The pore size may be the same or different in the core and outer layer of the chromatography media. The preferable exclusion limit in the outer layer depends on the size of the target protein. For example, if the target protein is influenza virus, the exclusion limit can be as large as 700 kDa, or even more.

If the target protein is a monoclonal antibody, a suitable exclusion limit is 100 kDa. Actual exclusion limits are however dependent on what flow rate that is used so the figures given for exclusion limits should only be interpreted as rough guidelines.

The ligands in the core which are capable of binding endotoxins, are preferably such as primary, secondary, tertiary or quaternary amines.

In a preferred embodiment the ligands are multimodal amines containing a hydrophobic moiety. Preferably the hydrophobic moiety consists of an aliphatic or aromatic hydrocarbon with 3-20 carbon atoms, preferably between 4 and 18 carbon atoms. Most preferably the ligands are octylamine.

The chromatography media may be made of a natural or synthetic polymer, preferably a natural polymer such as agarose.

The sample to be purified by the method of the invention may be any sample suspected of containing endotoxins and is especially suitable for a supernatant from a cell culture producing recombinant proteins, virus like particles or viruses. The method may also be suitable for removal of endotoxin from egg based production of virus.

BRIEF DESCRIPTION OF THE DRAWING

FIG. 1 illustrates a chromatogram of endotoxin removal according to the invention.

DETAILED DESCRIPTION OF THE INVENTION

The invention will now be described more closely in association with the drawings and some non-limiting examples.

In an embodiment of the invention, the invention relates to a method for endotoxin removal from a sample comprising the following steps: combining the sample comprising one or more target molecule(s) and an endotoxin with a chromatography media comprising beads having an inner porous core functionalized with ligands capable of binding the endotoxin and thick outer porous layer up to 7 μm thick (preferably 3-7 μm) without said functional groups and a pore size of the inner porous core being small enough to exclude the target molecule from the inner core, wherein the exclusion limit of said outer porous layer is up to 700 kDa (preferably about 100 kDa or 700 kDa); and collecting the sample from the media, wherein the sample comprises an endotoxin level which is at least 75% less, preferably 90% less, than before the removal and the yield of the target molecule is at least 75%. The target molecule being a virus (about 700 kDa) or a monoclonal antibody (about 100 kDa).

Materials and Methods

A Tricorn 5/20 column (Column volume (CV)=0.47 ml) was packed with Capto Core 700 (coarse filters) (GE Healthcare Bio-Sciences AB, Sweden). This media has a 5 μm outer porous layer without ligands and octylamine ligands in the core. The exclusion limit is around 700 kDa.

EXAMPLE 1

Endotoxin Removal

Fluorescence-labelled endotoxins were used in this test (Lipopolysaccharides, Alexa Fluor 594 conjugate (L23353 from Molecular Probes)). The endotoxins were dissolved in PBS and diluted to an end concentration of 1 μg/ml (which corresponds to 10000 U/ml if 0.1 ng=1 U was assumed). The solution was kept in the dark as much as possible to avoid degradation of the fluorophore. The chromatographic method described below was used.

| Step | Volume (CV) | Flow velocity (cm/h) | Buffer |
|---|---|---|---|
| Pre-equilibration | 5 | 300 | 20 mM Tris, pH 7.5 + 150 mM NaCl |
| Equilibration | 5 | 300 | PBS |
| Sample load | 144 | 50 | 1 μg/ml endotoxin in PBS |
| Wash | 5 | 300 | PBS |
| CIP | 5 | 50 | 1M NaOH + 27% 1-propanol |

Fractions of 2 CV were collected throughout the sample load. 200 μL of each fraction was transferred to a black microplate. A standard curve for the endotoxin (1, 0.5 and 0.25 μg/ml) was prepared in the same plate. The plate was read in a fluorometer with excitation: 590 nm and emission: 617 nm.

Results

The chromatogram from the experiment is shown in FIGURE. The concentration of endotoxin in the flow through fractions is represented by the solid line and the dashed curve represents the bound amount of endotoxin. The A 280 curve is represented by the dotted line. Approximately 90% of the total amount of endotoxin was bound to the core bead initially, which slowly decreased to about 80% towards the end of the experiment where totally ~1.25 million endotoxin Units/ml medium was bound.

EXAMPLE 2

Purification of Influenza Virus

To obtain a high yield of the target molecule is always one of the main goals of any purification step.

The particles of the present invention are well suited for the purification of viruses and give high yield while impurities can be removed since viral particles are significantly larger in size than most of the contaminants.

This is Illustrated in the Following Example.

Analysis Methods Virus

Concentration

The DotBlot HA assay was used according to a standard protocol.

DNA Concentration

The PICOGREEN® DNA assay was used according to the manufacturers instruction (available from lnvitrogen).

Protein Concentration

The Bradford protein assay was used according to the manufacturers instruction. (Available from Bio-Rad)

Sample

An influenza virus sample produced in-house was used in the study. The virus was propagated in MOCK cells until lysis occurred. Influenza virus strain A/HINI/Solomon Islands was used. After lysis, the material was concentrated-iox in an ultrafiltration (UF) step and another −2× in a diafiltration (DF) step (Hollow Fiber Cartridge 500 kDa). The diafiltration buffer was 50 mM Tris-HCl, 150 mM NaCl pH 7.3 and the sample was frozen until used.

Chromatography Method and Results

Column: 2 ml TRICORN™ 5/100 column packed with particles of the present invention with 7 µm thick neutral outer layer and octyl amine as ligand in the interior. The particles in this example are agarose particles and have an exclusion limit of around 700 kDa.

10 ml of influenza virus sample was applied at a flow rate of 75 cm/h. The flow-through fraction was collected.

The starting material and flow-through fraction was analysed for virus concentration, DNA concentration and protein concentration. The virus recovery, DNA depletion and protein depletion was calculated. The results are shown below.

Analysis Results

| Sample | Amount of virus [µg HA] | Amount of DNA [µg] | Amount of protein [µg] |
|---|---|---|---|
| Start Material | 600 | 555 | 4300 |
| Flow-through fraction | 582 | 233 | 780 |

Virus Recovery, Protein and DNA Depletion

| Sample | Amount of virus [µg HA] | Amount of DNA [µg] | Amount of protein [µg] |
|---|---|---|---|
| Start Material | 600 | 555 | 4300 |
| Flow-through fraction | 582 | 233 | 780 |

The virus recovery is high, 97%, for the particles of the present invention and standard buffers for virus purification where the virus is stable can be used without any optimisation. The protein depletion is also very good.

The endotoxin removal was not measured for this sample but essentially the same media was used for this and the previous example so it can be assumed to be of a similar level.

What is claimed is:

1. A method for endotoxin removal from a sample comprising the following steps: combining the sample comprising one or more target molecule(s) and an endotoxin with a chromatography media comprising beads having an inner porous core functionalized with ligands capable of binding the endotoxin and a outer porous layer up to 7 pm thick without said functional groups and a pore size of the inner porous core being small enough to exclude the target molecule from the inner core, wherein the exclusion limit of said outer porous layer is about 100 kDa; and collecting the sample from the media, wherein the sample comprises an endotoxin level which is at least 75% less, preferably 90% less, than before the removal and the yield of the target molecule is at least 75%.

2. The method of claim 1, wherein the outer porous layer is 3-7 pm thick.

3. The method of claim 1, wherein the chromatography media is packed in a column and the sample is collected in the flow-through.

4. The method of claim 1, wherein the target molecule is a monoclonal antibody.

5. The method of claim 1, wherein the core is functionalized with ligands capable of binding endotoxins such as primary, secondary, tertiary or quaternary amines.

6. The method of claim 1, wherein the ligands are multimodal amines containing a hydrophobic moiety.

7. The method of claim 6, wherein the hydrophobic moiety consists of an aliphatic or aromatic hydrocarbon with 3-20 carbon atoms, preferably between 4 and 18 carbon atoms.

8. The method of claim 7, wherein the ligand is octylamine.

9. The method of claim 1, wherein the chromatography media is made of a natural or synthetic polymer.

10. The method of claim 1, wherein the sample is a supernatant from a cell culture producing recombinant protein or virus.

11. A method for endotoxin removal from a sample comprising the following steps: combining the sample comprising one or more target molecule(s) and an endotoxin with a chromatography media comprising beads having an inner porous core functionalized with ligands capable of binding the endotoxin and an outer porous layer up to 7 pm thick without said functional groups and a pore size of the inner porous core being small enough to exclude the target molecule from the inner core, wherein the exclusion limit of said outer porous layer is about 700 kDa; and collecting the sample from the media, wherein the sample comprises an endotoxin level which is at least 75% less, preferably 90% less, than before the removal and the yield of the target molecule is at least 75%.

12. The method of claim 11, wherein the outer porous layer is 3-7 pm thick.

13. The method according to claim 11, wherein the chromatography media is packed in a column and the sample is collected in the flow through.

14. The method of claim 11, wherein the target molecule is a virus.

15. The method of claim 11, wherein the core is functionalized with ligands capable of binding endotoxins such as primary, secondary, tertiary or quaternary amines.

16. The method of claim 11, wherein the ligands are multimodal amines containing a hydrophobic moiety.

17. The method of claim 16, wherein the hydrophobic moiety consists of an aliphatic or aromatic hydrocarbon with 3-20 carbon atoms, preferably between 4 and 18 carbon atoms.

18. The method of claim 17, wherein the ligand is octylamine.

19. The method of claim 11, wherein the chromatography media is made of a natural or synthetic polymer.

20. The method of claim 11, wherein the sample is a supernatant from a cell culture producing recombinant protein or virus.

* * * * *